(12) United States Patent
Subotics (10) Patent No.: US 7,155,268 B2
(45) Date of Patent: Dec. 26, 2006

(54) NON-INVASIVE MEASUREMENT OF BLOOD GLUCOSE LEVEL

(75) Inventor: Gyula Subotics, Budapest (HU)

(73) Assignee: Iris Medical Technologies International Ltd., Alberta (CA)

( * ) Notice: Subject to any disclaimer, the term of this patent is extended or adjusted under 35 U.S.C. 154(b) by 239 days.

(21) Appl. No.: 10/494,485

(22) PCT Filed: Oct. 31, 2002

(86) PCT No.: PCT/CA02/01678

§ 371 (c)(1),
(2), (4) Date: Oct. 21, 2004

(87) PCT Pub. No.: WO03/037174

PCT Pub. Date: May 8, 2003

(65) Prior Publication Data

US 2005/0065416 A1 Mar. 24, 2005

(30) Foreign Application Priority Data

Oct. 31, 2001 (HU) .................................. 0104610

(51) Int. Cl.
*A61B 5/00* (2006.01)
(52) U.S. Cl. ........................ 600/319; 600/318
(58) Field of Classification Search ................ 600/310, 600/316, 318, 319; 351/200, 223
See application file for complete search history.

(56) References Cited

U.S. PATENT DOCUMENTS 5,713,353 A * 2/1998 Castano ...................... 600/319

6,113,537 A  9/2000 Castano

FOREIGN PATENT DOCUMENTS

GB  990222  4/1965

OTHER PUBLICATIONS

Kurtenbach A. et al: "Preretinopic Changes in the Colour Vision of Juvenile Diabetics" British Journal of Ophthalmology, London, GB, vol. 83, No. 1. Jan. 1999, pp. 43-46, XP001148306, ISSN:0007-1161.
Kurtenbach A. et al. "Development of Brightness Matching and Colour Vision Deficits in Juvenile Diabetics". Vision Research, Pergamon Press, Oxford, GB, vol. 39, No. 6, Mar. 1999, pp. 1221-1229, XP001148167, ISSN: 0042-6989.

* cited by examiner

*Primary Examiner*—Eric F. Winakur
*Assistant Examiner*—Jack Lin
(74) *Attorney, Agent, or Firm*—Simpson & Simpson, PLLC (57) ABSTRACT

A non-invasive device for measuring blood glucose levels comprises an enclosure with a cover and dual openings, wherein the enclosure is covered with a transparent material (e.g., glass or plastic); at least two test cards arranged at specified distances and positioned within the enclosure; an illuminator and a conical light reflecting surface for casting a beam on the test cards. Light from one test card is reflected through one of the dual openings to sensing receptors of one eye. In order to enable the part of a diffuse beam reflected from the second test card made parallel within 10° to fall on the sensing receptors of the second eye, the enclosure is provided with a tubular prism covered with a closing plate having an opening at a first end while having an opening covered preferably with transparent material at a second end.

10 Claims, 10 Drawing Sheets

NON-INVASIVE MEASUREMENT OF BLOOD GLUCOSE LEVEL

CROSS REFERENCE TO RELATED APPLICATIONS

The present application claims benefit to International Application PCT/CA02/01678, filed Oct. 31, 2002, said International Application claims priority from Hungarian Application P0104610, filed Oct. 31, 2001.

BACKGROUND OF THE INVENTION

1. Field of the Invention

The present invention relates to a non-invasive device for determining blood glucose levels through the measurement of colour perception.

2. Description of the Prior Art

Diabetes mellitus is a disease which afflicts millions of individuals throughout the world. It is a chronic metabolic disorder that is characterized by a high blood glucose concentration, otherwise known as hyperglycaemia. Elevated glucose levels are brought about by insulin deficiencies and/or insulin resistance. Hyperglycaemia occurs as a result of uncontrolled hepatic glucose output, in addition to a reduction of glucose uptake by skeletal muscle. If the threshold for renal glucose re-absorption is exceeded, a number of negative physiological outcomes can occur including, an increase in urine glucose levels and osmotic diuresis, a condition which leads to dehydration and excessive thirst. As the disease progresses, individuals afflicted with diabetes may experience damage to their kidneys retina and peripheral nerves.

As a result of the potential negative effects of the disease, diabetes sufferers must take frequent measurements of the blood glucose levels, in order to monitor and control said glucose levels. Based on the results of these measurements, individuals can alter their food intake, physical activities, and insulin dosage, as a means of regulating blood glucose levels.

A number of methods and devices for measuring blood glucose levels are disclosed in the prior art. However, the majority of these means of blood glucose measurement are characterized by their invasiveness and their cost.

One such blood-glucose level measuring device, the D CONT Cabrio, requires an individual to perform the invasive step of pricking their finger in order to draw blood for testing. Puncturing of the finger can be quite painful and can result in significant discomfort for the individual. After blood has been drawn, a drop of blood from the finger is applied to a test strip, which is then inserted into an electronic glucose measuring device. Upon insertion in the measuring device, a chemical reaction occurs between the blood and the test strip, which results in the test strip changing colour based on the level of glucose present in the blood. Colour changes are detected by the electronic glucose measuring device and results are displayed as numeric values representative of the level of blood glucose. In addition to the aforementioned discomfort caused by this method of testing, the test strips used in this methodology are not always available in a sufficient quantity, and the cost of purchasing such strips can represent a large financial burden on the individual. Further, the purchase cost of the actual measuring device is also quite high, therefore, patients of limited financial means may not be able to afford the device.

Non-invasive, blood glucose level testing devices have also been described in the prior art, but such devices are also characterized by specific deficiencies. For example, the Gluco-Watch is one such device designed to eliminate the need for invasive blood glucose testing. The Gluco-Watch is worn on the arm of a patient and is equipped; with sensors that can measure blood glucose levels at intervals of 3 hours. Unfortunately, this device is also costly to the consumer.

The present invention seeks to provide a device for testing blood glucose levels that overcomes the deficiencies in the prior art. Specifically, the present invention provides a non-invasive measurement device, at a reasonable cost to the consumer.

SUMMARY OF THE INVENTION

The present invention relates to a blood-glucose level measuring device enclosed in a box (19) that can be opened and closed, and that has a cover (39) provided with two openings (9, 12) covered with some transparent material and is made preferably of dye-cast plastic, characterized in that at least two test cards (1, 2) are arranged at specified distances and specified positions within the box (19), and at least one illuminator (17) is built in the box preferably in front of a conical reflecting surface (18); in order to enable the diffuse beam that is generated by the illuminator, reflected from the inner surface of the closed box (19) to illuminate the two test cards (1, 2) and reflected from one of the test cards (1) to fall on the sensing receptors of the eye (6), the box (19) is provided with an opening (12) covered preferably with some transparent material, while in order to enable the part of diffuse beam (4) reflected from the other test card (2) made parallel preferably within 10° to fall on the sensing receptors of the eye (5), the box is provided with a tubular prism (10) that is covered with a closing plate (7) with an opening (8) at the one end while having an opening (9) covered with some preferably transparent material at the other end.

BRIEF DESCRIPTION OF THE DRAWINGS

These and other features of the preferred embodiments of the invention will become more apparent in the following detailed description in which reference is made to the appended drawings wherein.

DESCRIPTION OF THE PREFERRED EMBODIMENTS

In a preferred embodiment, the present invention provides a non-invasive blood glucose level testing device that measures the level of blood glucose, utilizing an optical based test.

The preferred device can be used by individuals suffering from diabetes, said individuals having to control their blood glucose level through regular injections of insulin. In addition, the preferred device can also be used for preventative purposes. The preferred blood-glucose level measuring device allows for detection of increased blood glucose levels before such levels exceed safe physiological limits.

In a preferred embodiment, the blood-glucose level testing device is based on the principle that fluctuations in blood-glucose levels can dramatically influence eyesight. For example, during fluctuations in blood-glucose levels, because of the fact that the retina is highly sensitive to said fluctuations, the perception of an observed image and its color may be altered. As such, an individual may be able to directly assess the extent of vision changes and estimate such changes quantitatively, using a preferred embodiment of the disclosed invention.

Experiments have shown that blood-glucose level is interconnected with color perception. People with different blood-glucose levels perceive the same color differently, and if the color perception of the two eyes is changed simultaneously, the current blood-glucose level can be determined from this difference using Table 1, which is based on experimental results.

TABLE 1

| The sign of the color by the color-scale 1 | The sign of the color by the color-scale 1/A | Blood-glucose level (mmol/litre) |
|---|---|---|
| S 2040-Y90R | S-1080-R | 3 |
| S 2050-R | S-1080-R | 5 |
| S 2050-Y90R | S-1080-R | 6 |
| S 1070-R | S-1080-R | 8 |
| S 3050-R30B | S-1080-R | 12 |

The larger the difference between the color perception of the eyes, the more precisely the blood-glucose level can be determined. Experiments also showed that while watching a shade of color through a low-diameter hole with one eye, the other eye perceives a different shade. This difference can be enhanced using a tube with an arbitrary bore as a small hole, and the other end, positioned away from the eye, of the tube the bore is reduced, for example to 0.5 mm.

The experiments performed demonstrated that, if the photo-receptors of the eye receive diffuse light reflected from a color object, the extent of modification in the color sensing, due to the change in the blood-glucose level, is magnified by collecting the diffuse light beam into a nearly parallel beam. By comparing the color effects caused by the diffuse light reflected from a color object, with those caused by the parallel beam on the photo receptors, as well as allocating the blood-glucose level value at the time of measurement to the color difference estimated quantitatively, and then repeating the measurements with different blood-glucose level values, the possibility of establishing a blood-glucose level scale based on color sensing was obtained. The aforementioned scale can be used to determine blood-glucose levels without requiring any blood samples and is therefore non-invasive.

Color objects, color test cards, colors projected on white cards, colors generated in electric way, colors generated by means of liquid crystals, can also be used for color sensing for the purpose of blood glucose level measurement.

In a preferred embodiment, as described further below, a blood-glucose level measuring device was produced that is enclosed in a box (19) that can be opened and closed. The device has a cover (39) provided with two openings (9,12) covered preferably with transparent material (e.g. glass, plastic) and is made preferably of dye-cast plastic, where, according to the invention, at least two test cards (1,2) are arranged at specified distances and specified positions within the box (19), and at least one illuminator (17) is built in the box preferably in front of a conical reflecting surface (18). In order to enable the diffuse beam that is generated by the illuminator, reflected from the inner surface of the closed box (19) to illuminate the two test cards (1,2) and reflected from one of the test cards (1) to fall on the sensing receptors of the eye (6), the box (19) is provided with an opening covered preferably with some transparent-material, while in order to enable the part of diffuse beam (4) reflected from the other test card (2) made parallel preferably within 10 degrees to fall on the sensing receptors of the eye (5), the box is provided with a tubular prism (10) that is covered with a closing plate (7) with an opening (8) at the one end while having an opening (9) covered with some preferably transparent material at the other end.

Preferably, the test cards (1,2) paired appropriately, are fastened on the sides of a regular polygonal prism (21) that can be rotated within the blood-glucose level measuring device; a positioning spring holds the prism in its proper position and the blood glucose level value is indicated by the blood glucose indicator on the dial of the turn-knob.

It is preferred that the illuminator (17) of the blood-glucose level measuring device is actuated by a micro switch that is mounted between two springs fastened to the base plate of the box and fastened preferably to the upper spring when the turn knob is rotated.

Also in preferred embodiment, the illumination required for the blood-glucose level measuring device, is provided in the form of a glow lamp. The glow lamp is operated by a push-button switch or a rotating switch, and the illumination is active for a pre-determined time (e.g. 5 seconds) and, following this period, the illumination is disabled for a specified time (e.g. 4 seconds). When the device is ready to be switched on again, an indicator light is turned on. The device can be turned OFF and ON by a general switch.

In a preferred embodiment the blood-glucose level-measuring device is provided with a supply voltage indicator.

Figure 1:
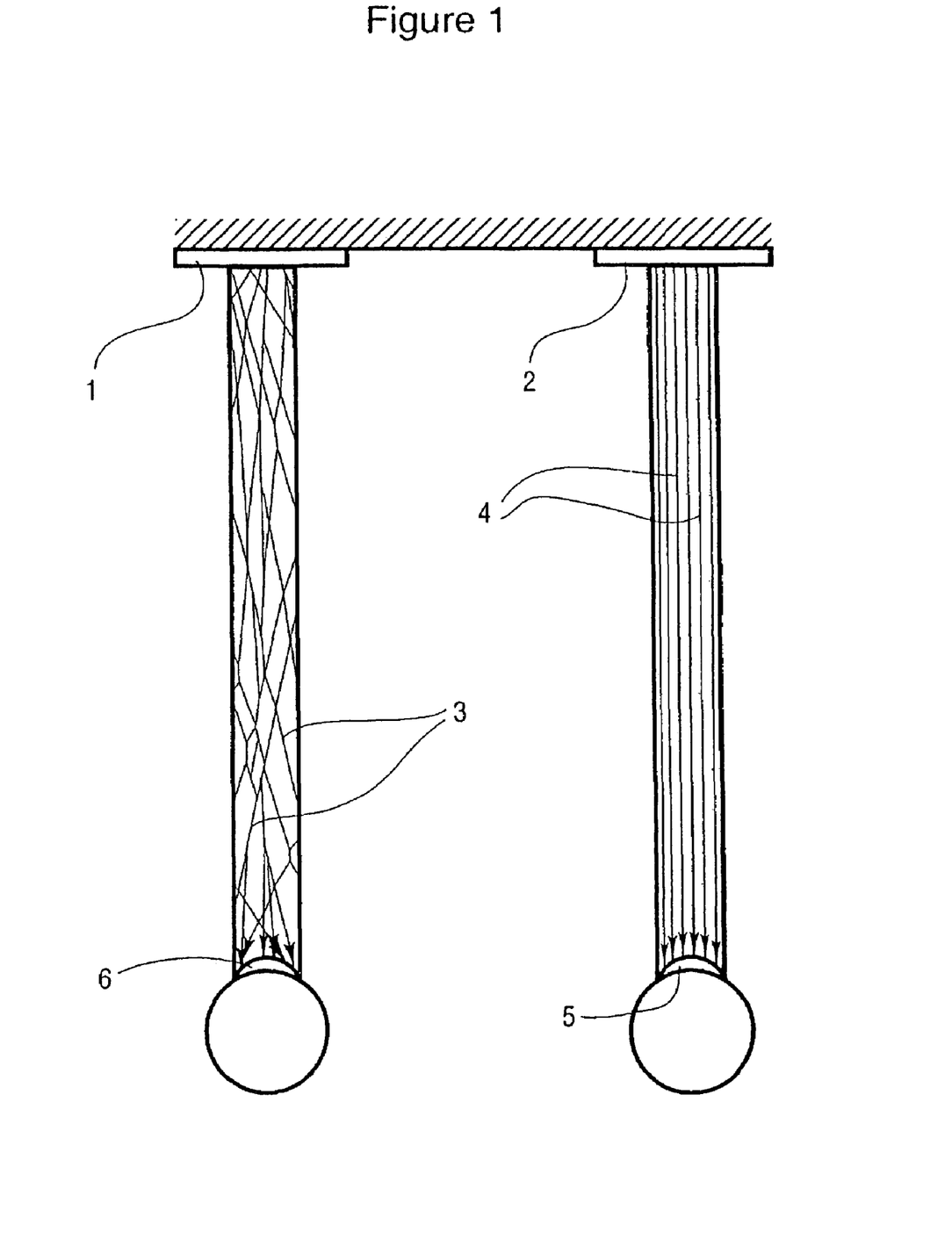
FIG. 1 diagrammatically shows the diffuse and parallel light beams reflected from two test cards located side by side and eyes.

Referring now to FIG. 1 of the accompanying drawings, there is shown diffuse light beams 3 and parallel light beams 4 reflected from test cards 1 and 2, towards eyes 6,5. During experimentation it was determined that diffuse light beams 3 and parallel light beams 4, reflected from the test cards 1 and 2, respectively, were perceived as the same color in individuals with a 5 mmol/liter blood-glucose level. For example, the colour Ral 1004 golden-yellow was perceived by both eye 6 exposed to the diffuse light beams 3, and eye 5 exposed to the parallel light beams. However, when an individual had a blood glucose level of 8 mmol/liter, Ral 1004 golden yellow was perceived to be golden yellow with diffuse light, while it is perceived to be of Ral 8008 olive brown colour with parallel light. As a result, if parallel light beams 4 reflected from a test card of RAL 1004 color arrive at eye 5, and diffuse light beams 3 reflected from a test card of RAL 8008 color arrives at eye 6, both of the test cards would be perceived to be a RAL 8008 olive-brown color.

Figure 2:
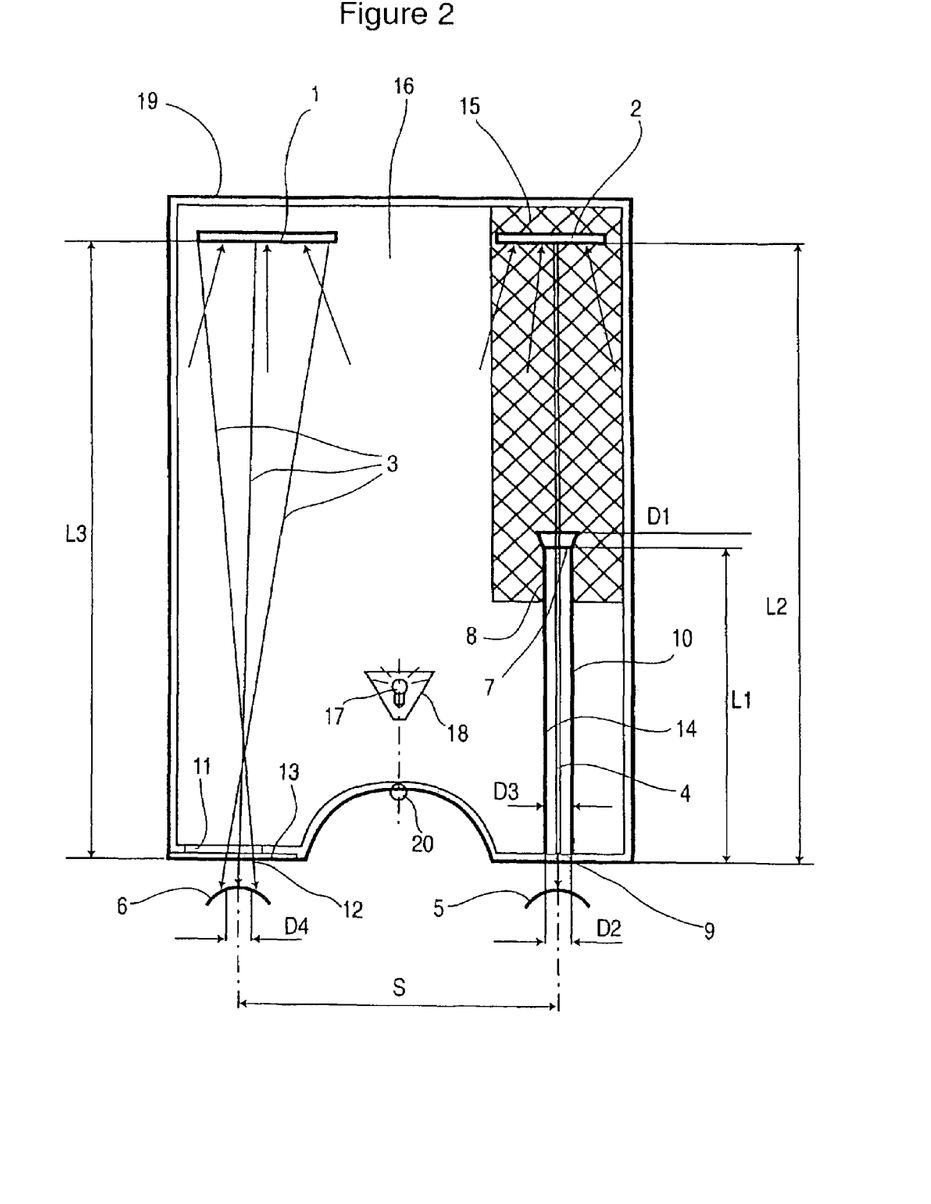
FIG. 2 diagrammatically shows an embodiment of the blood glucose-level measuring device.

Referring now to FIG. 2 of the accompanying drawings, there is shown a view of a preferred embodiment of the blood-glucose level measuring device in an open state. The inner space 16 of box 19, of a preferred blood-glucose level measuring device is illuminated by the illuminator 17. The illuminator 17 is surrounded by a conical light reflecting surface 18, which directs beams of light towards the, preferably, coloured test cards 1,2. The coloured test cards 1 and 2 reflect light through openings 12 and 9, which are covered with transparent material, to eyes 5 and 6. The beams of light 3 reflected from the test card 1 are diffuse, while the light beams 4 reflected from test card 2 are nearly parallel. In other words, the reflected light beams 4 are allowed to deviate by up to 5° from the vertical. The parallel light beams 4, arrive at eye 5 through the opening 8 of closing plate 7, which covers the end of the tubular prism 10, and through opening 9, which is covered with transparent, material on the box 19. In order to enhance the purity of the appearing color, it is also necessary that inner surface 14 of the tubular prism 110 is comprised of a material with strong light absorbing properties. In addition, in a preferred embodiment, the light beams illuminating the test card 2 are shielded with a shielding 15 made of semi-transparent. (ie. opaque) material. Such shielding is required if the test card 2 has a bright surface.

Because a distance (S) of the pupils of each individual varies, the position of the openings 12 and 9 can be adjusted by means of the oval shaped opening 11 on the box 19. In addition, sliding plate 13 can be displaced and fastened, in order to ensure that the diffuse and parallel light beams can be sensed by the 5, 6 eyes. The illuminator 17 operates only if the electronic unit activates the LED 20. When the device is ready to measure blood-glucose levels a green light on the LED 20 turns on. When the green light turns on, the 17 illuminator can be switched on and blood-glucose level measurement intiated.

It is preferred that the diameter D1, of the preferably circular opening arranged on the closing plate of the tubular prism built into the blood-glucose level measuring device, is of up to 2 mm, while the diameter D2 of the preferably circular opening covered with some transparent material, as well as the diameter D4 of the preferably circular opening arranged on the slide plate, and covered with transparent material, are less than 10 mm each, and the diameter D3 of the tubular prism (10) is greater than or equal to the diameter D2.

Figure 3:
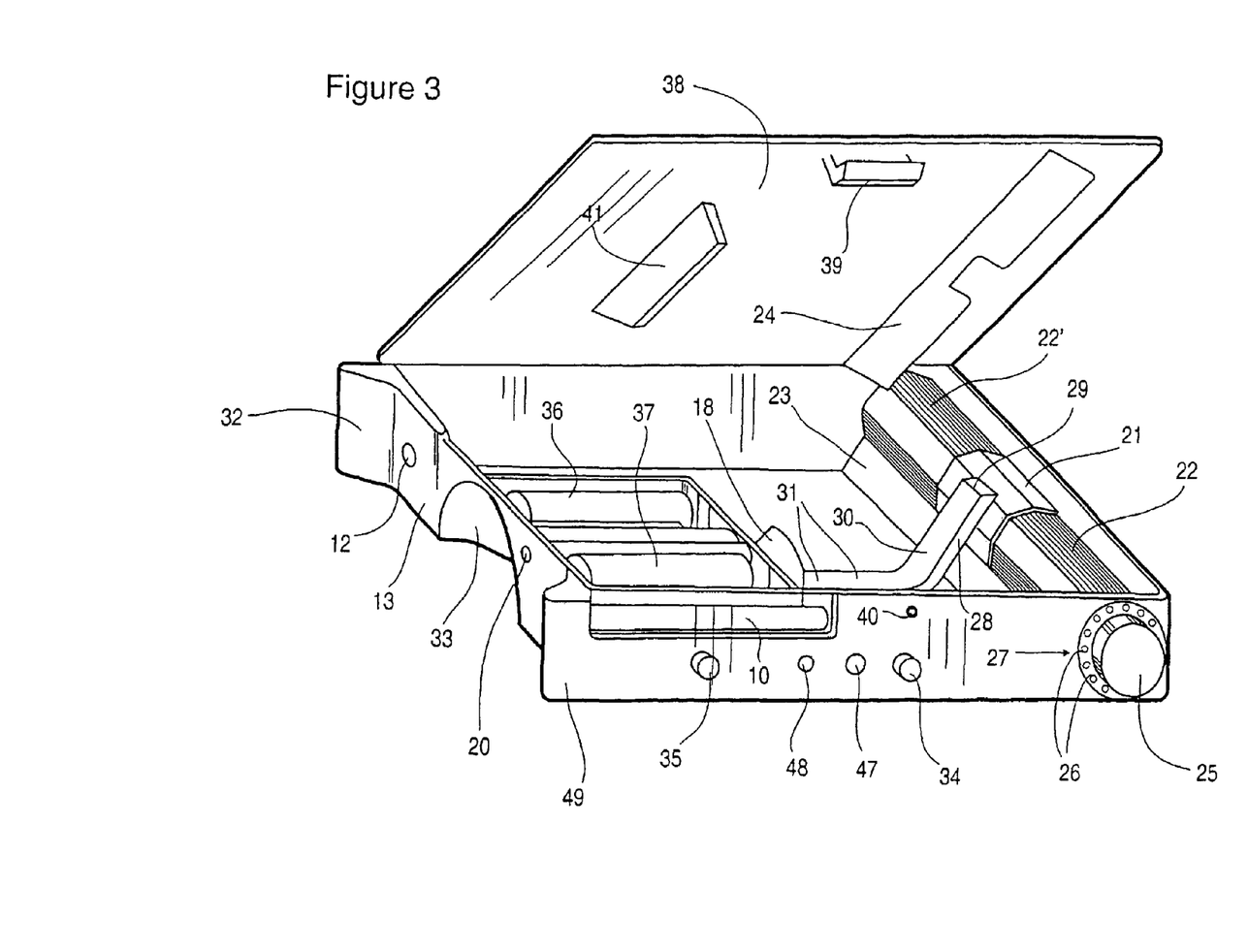
FIG. 3 diagrammatically shows an embodiment of the present invention comprising a revolving blood-glucose level indicator for accommodating several test cards, and further comprising a closing cover.

Referring now to FIG. 3 of the accompanying drawings an additional embodiment of the preferred blood-glucose measuring device is provided. In this embodiment a preferred blood-glucose level measuring device is provided with a revolving blood-glucose level indicator and lockable cover plate 38. Several test cards 22, 22', can be fitted to a decahedral regular prism 21, which can be rotated and is built into the lockable box 19. Paired test cards 22, 22' are fastened to the sides of the prism 21. It is preferred that the test cards not in use during the blood-glucose level measurement are covered by two cover plates 23, 24 in order to eliminate their disturbing effects. The regular prism 21 can be rotated using turn knob 25. The rim of the turn knob 25 is provided with a dial 26 suitable for indicating the blood-glucose level. The blood-glucose level is shown on the blood-glucose level indicator 27. Turning the regular prism 21 by a unit angle, its positioning is ensured by the positioning spring 28.

Spring 30, which is connected to and responsible for positioning the micro switch 29, is fastened to the bottom plate of lockable box 19 by fastening element 31. Between the two springs, the micro switch 29 is arranged and is fastened to the spring 30. The lockable box 19 is provided with dimming rims 32 arranged symmetrically. In order to ensure the comfortable use, the preferred embodiment has an indent 33 corresponding to the shape of a nose ridge. In order to ensure portable operation, the device is provided with rechargeable batteries 36 and 27, and a connector 47 for recharging. The readiness of the device to repeat the blood-glucose level measurement is indicated by the green light of the 20 LED. When the batteries 36 and 37 require recharging, a red light or, voltage indicator 48 is switched on. The device can be switched off and on by using general switch 34. The repeated measurements can be initiated by means of touch-switch 35. The cover plate 38 is fastened to the box 19 by means of closing element 39, while it can be opened through opening hole 40. The undesired displacement of batteries is prevented fastening element 41.

Figure 4:
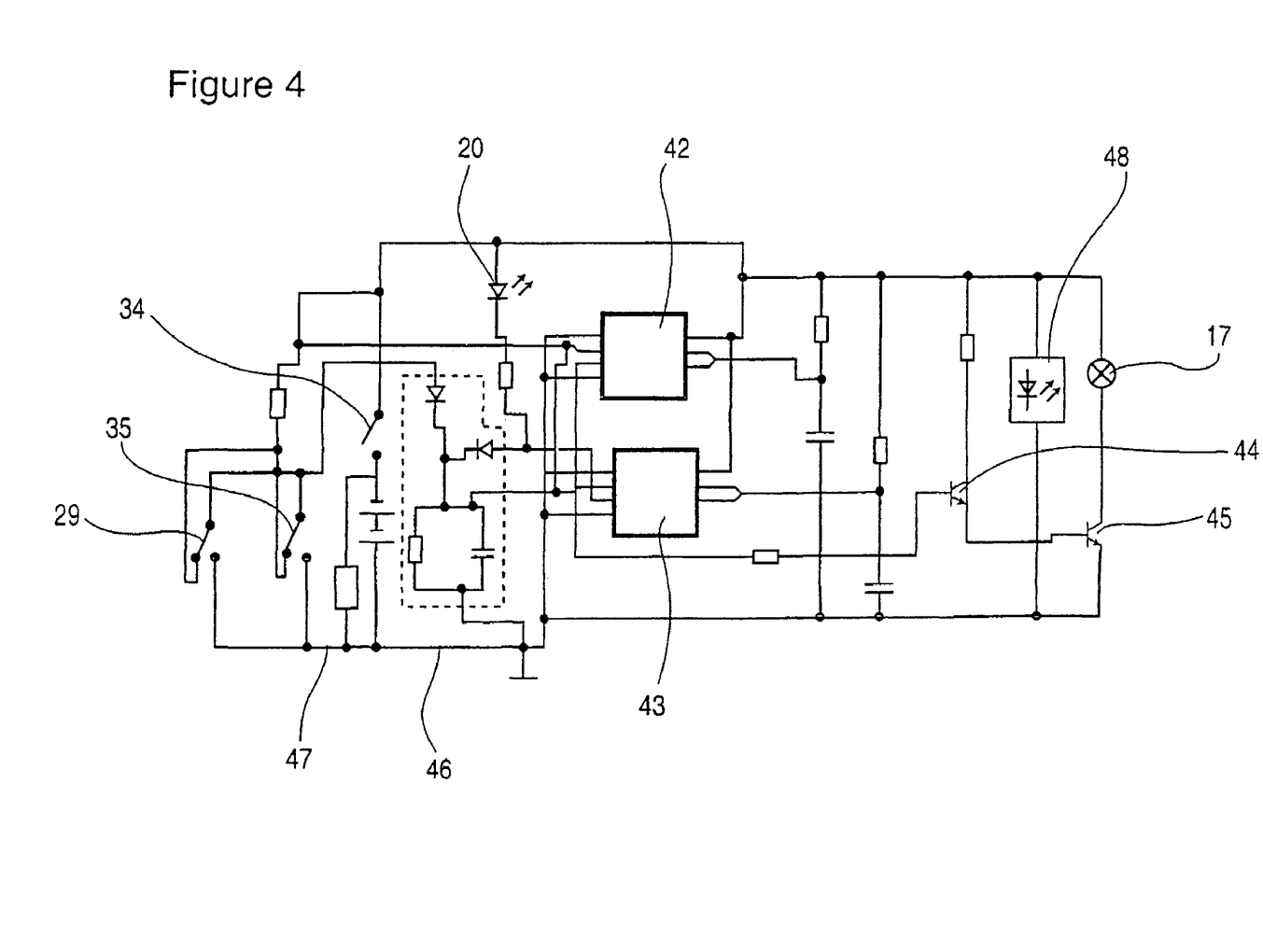
FIG. 4 diagrammatically shows a detailed schematic of the electric circuit utilized in the blood-glucose level measuring device.

Referring now to FIG. 4 of the accompanying drawings a preferred embodiment of the electric circuit of the preferred blood-glucose measuring device is provided. The internal illumination of the blood-glucose level-measuring device can be ensured for a specified time (e.g. 5 seconds) by means of the illuminator 17, said illuminator being activated by touch-switch 29 and touch-switch 35, respectively. A further requirement for the evaluation of blood-glucose level measurement is that the re-activation of the device is prevented for a specified time (e.g. 5 seconds) following each measurement. When the preferred device is ready for operation, its status is indicated by the green light of LED 20. For the measurement of time, the monostable 42, 42 or in other words timing circuit (e.g. IC of type C556), is utilized. On activating the push-button 35 or the turn knob 29 switch, both monostables 42 and 43 receive a voltage pulse necessary for tripping. The operating time of monostable 42 is approximately 5 seconds. The output from monostable 42 drives through the power amplifier 44 and 45 (T1 and T2 transistors in Darlington circuit) and the illuminator 17. The monostable 43 prevents the device from being re-started during the operation of the illuminator 17, and for 5 seconds following operation. As a result a time cycle of 10 seconds is controlled by the monostable 43, the output signal of which is fed back through the OR gate 46 to the starting input of the timing circuits 42 and 43.

To the other input of the OR gate 46, push button 34 and the turn knob switch 29 are connected in parallel. As a result of the operation of the 46 OR gate, the timer circuit 42 is allowed to be re-started only if a 10-second operation of the 43 timer circuit is completed, and either the push-button 35 or the turn knob switch 29 is operated. The possibility of re-starting the device is indicated by the LED 20, connected to the output of the timer circuit 43, that operates for 10 seconds, and following the expiry of the 10-second period, it activates the LED 20. Once the conditions of re-starting are fulfilled, the LED 20 is switched off.

The preferred blood-glucose level measuring device can be produced at low cost and is extremely simple to use. Further, no additional materials and supplies are required for operation of the device after its initial purchase.

Figure 5:
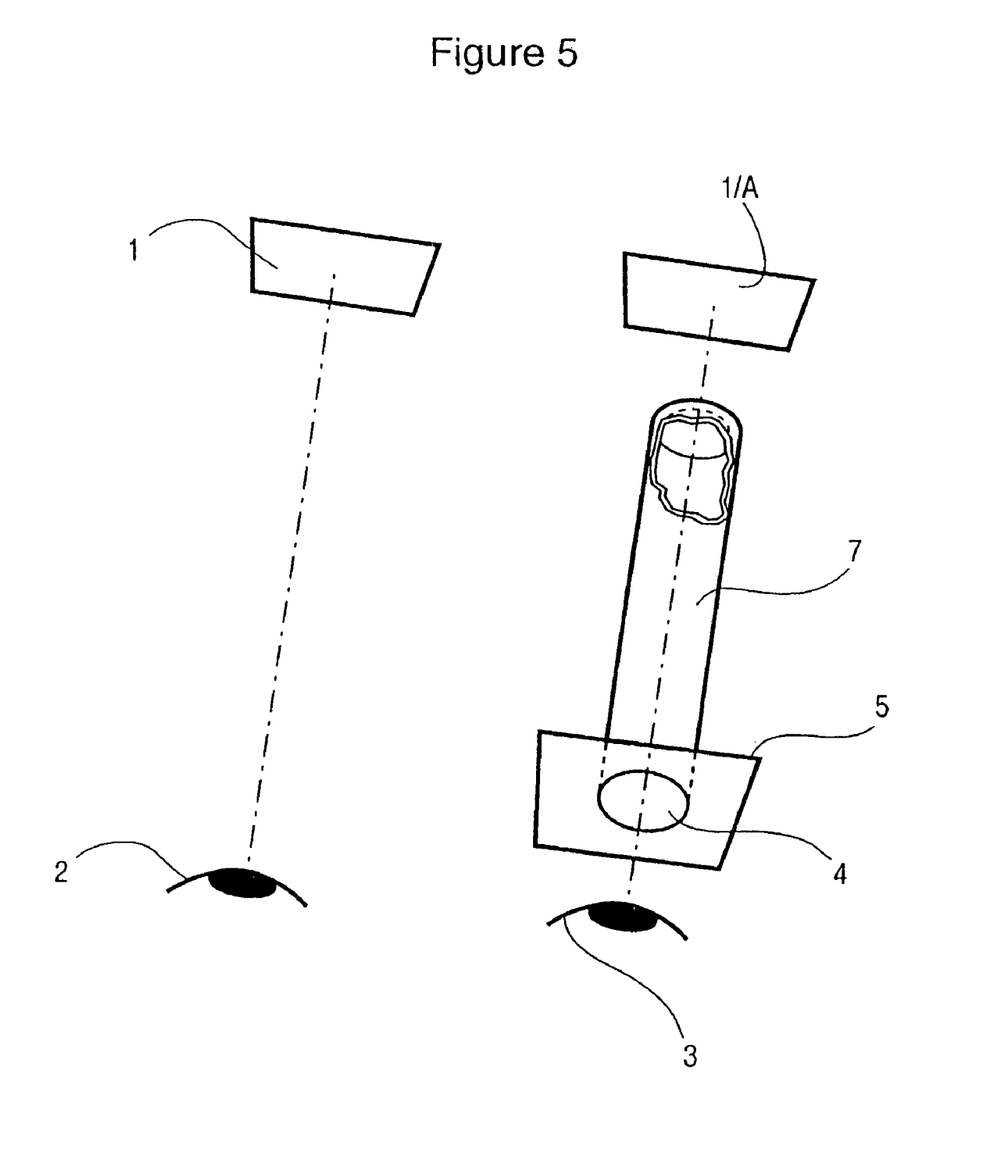
FIG. 5 diagrammatically shows the device formed by the invention
Figure 6:
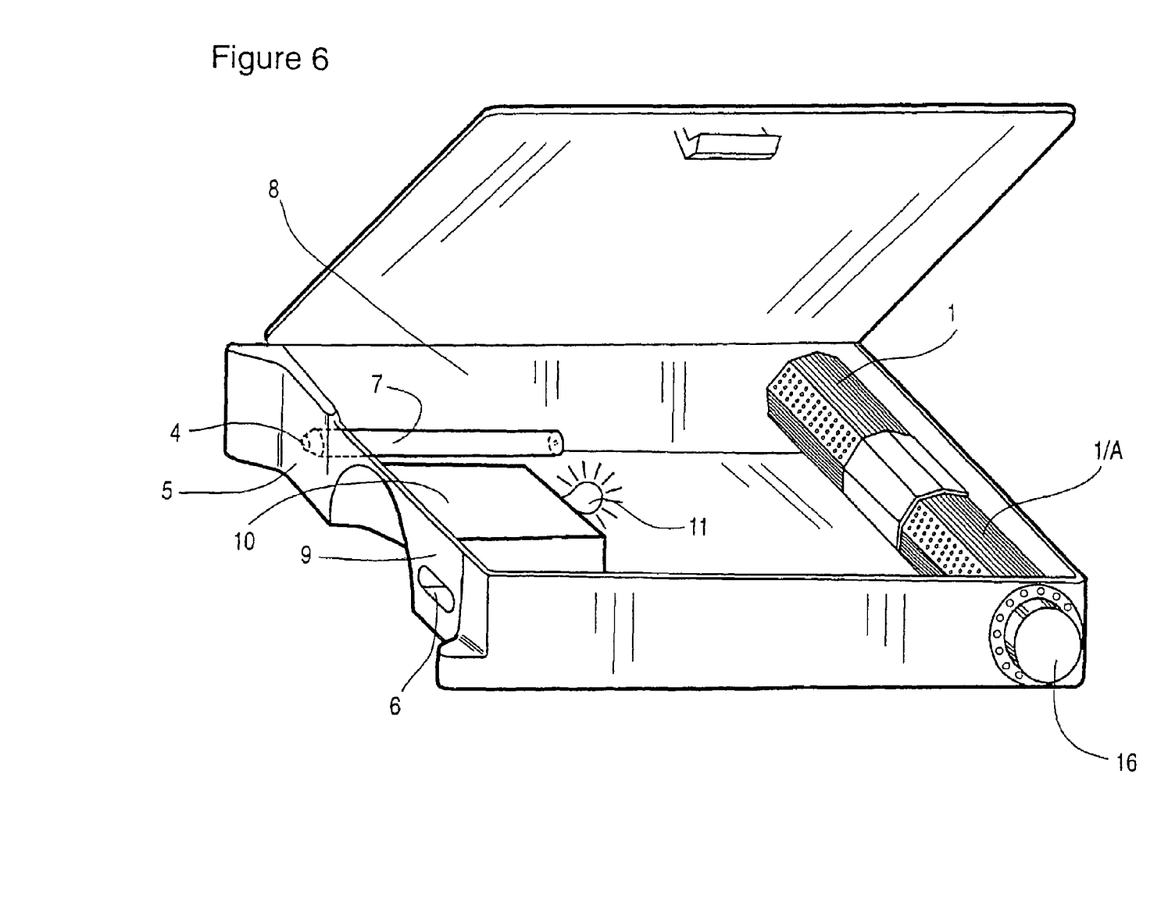
FIG. 6 diagrammatically shows the device composed by the invention in the box FIG. 7 diagrammatically shows the device in an adjustable form.

FIGS. 5 and 6 show the preferred device has a color-scale (1, 1/A) and in front of that a looking appliance (5) formed to eyehole (4) which covers the eye (3). The (1) color-scale is composed to have a view of it with naked eye. The tube joins to the opening of looking appliance, the inside bore of its open end is 0.5 mm.

By the one device of the invention there are two color-scales (1, 1/A) side by side and they can rotate with the adjusting knob (16). There are 11 bulbs in front of the color-scales (1, 1/A) and 10 energy source, for example penlight battery, is intended for them. The color-scales can use as artificial light for example LED.

Figure 7:
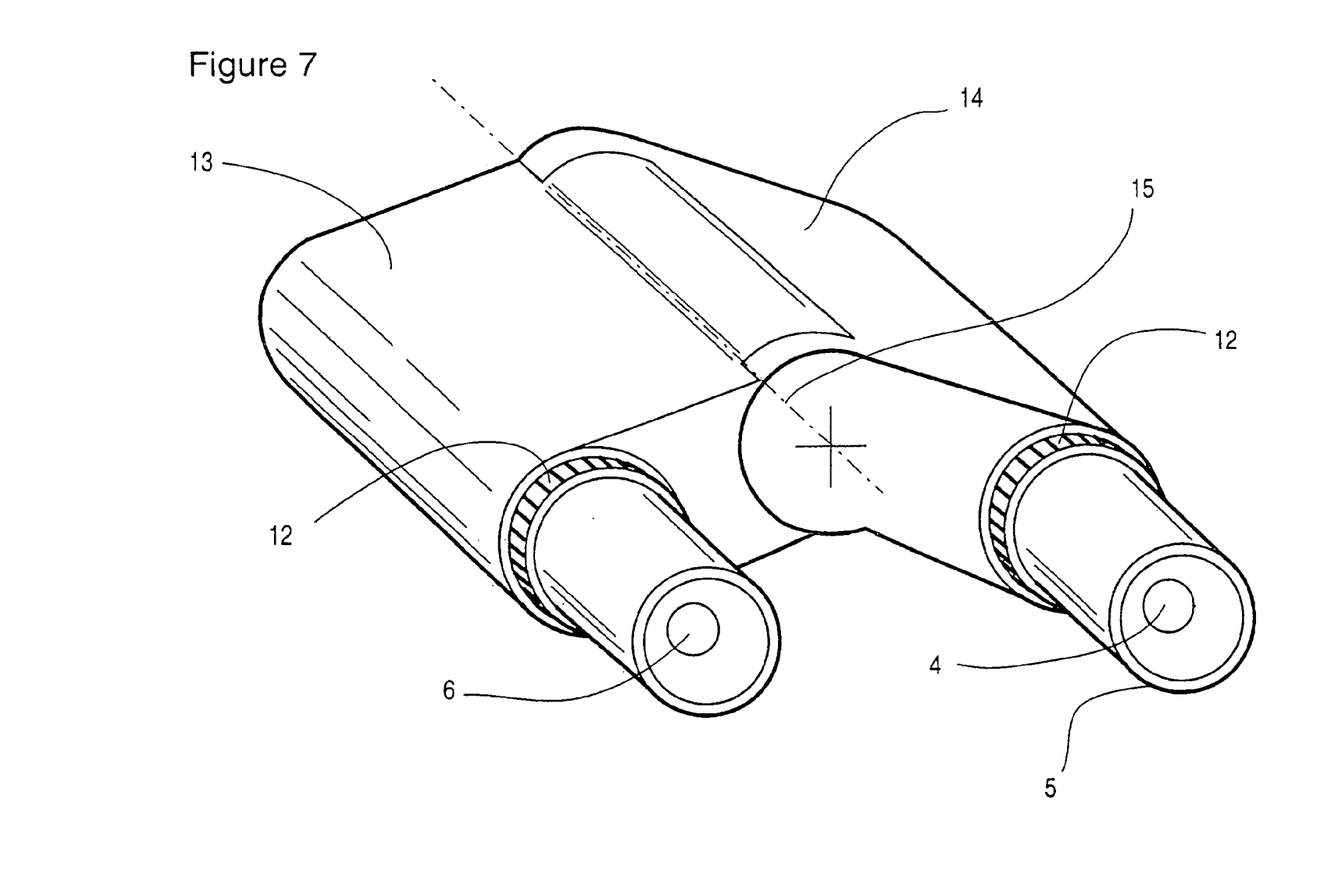
Figure 8:
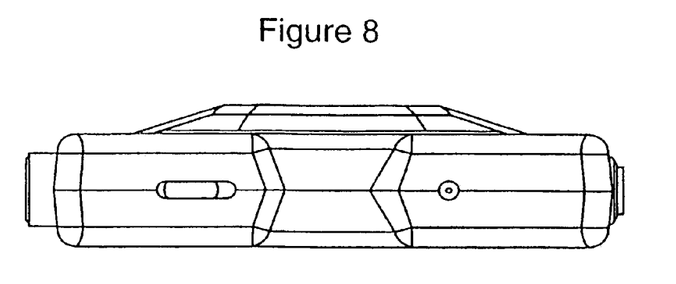
FIG. 8 diagrammatically shows a detailed side view of one side of the present invention FIG. 9 diagrammatically shows a detailed side view of a second side of the present invention FIG. 10 diagrammatically shows a detailed schematic of the present invention comprising a revolving blood-glucose level indicator for accommodating several test cards.
Figure 9:
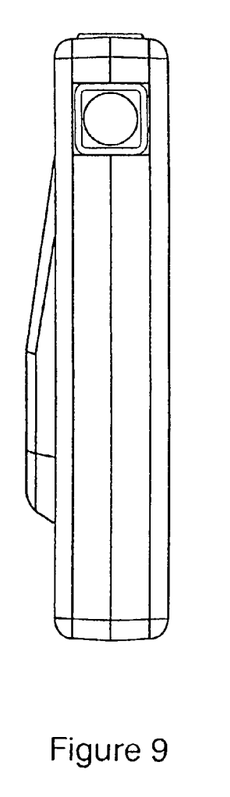
Figure 10:
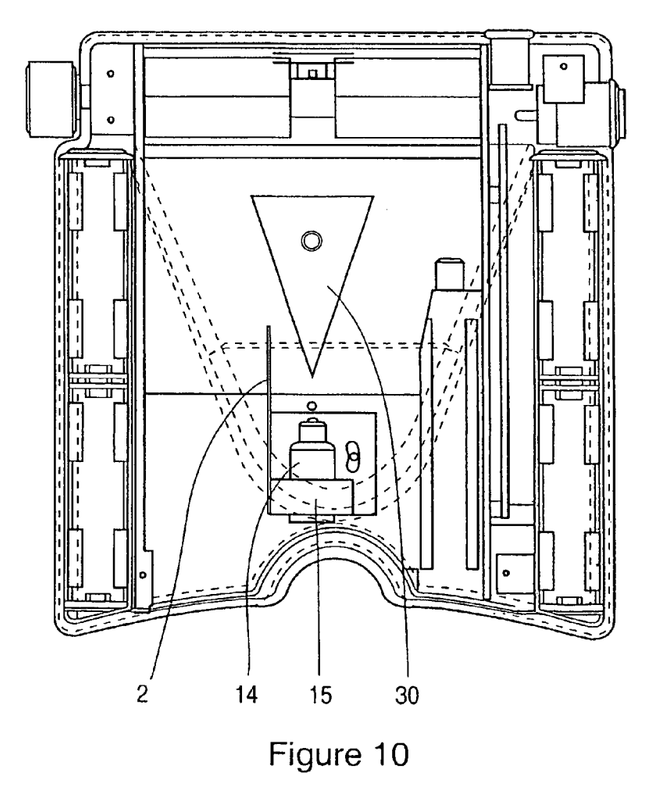
Figure 11:
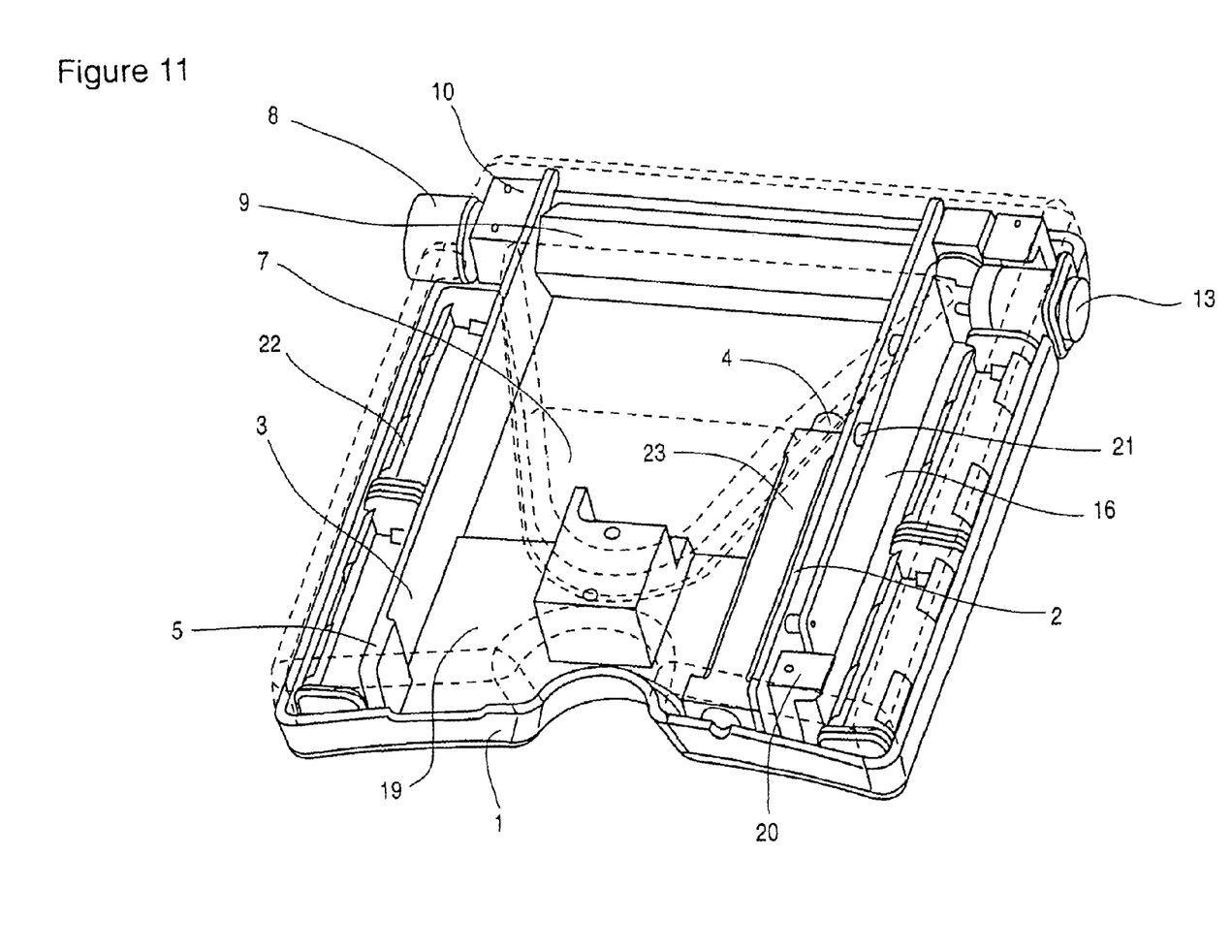
FIG. 11 diagrammatically shows an additional detailed schematic of the present invention comprising a revolving blood-glucose level indicator for accommodating several test cards.
Figure 12:
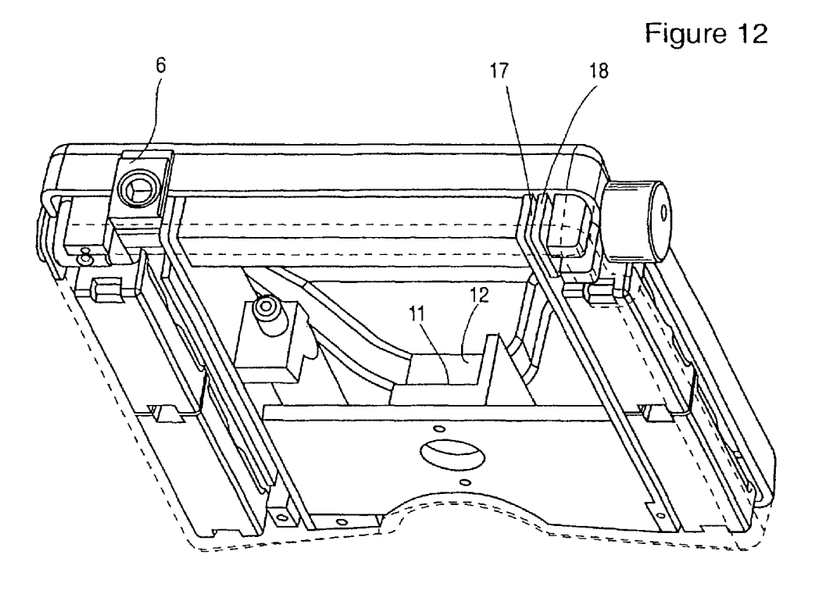
FIG. 12 diagrammatically shows an additional detailed schematic of a preferred embodiment of the present invention.
Figure 13:
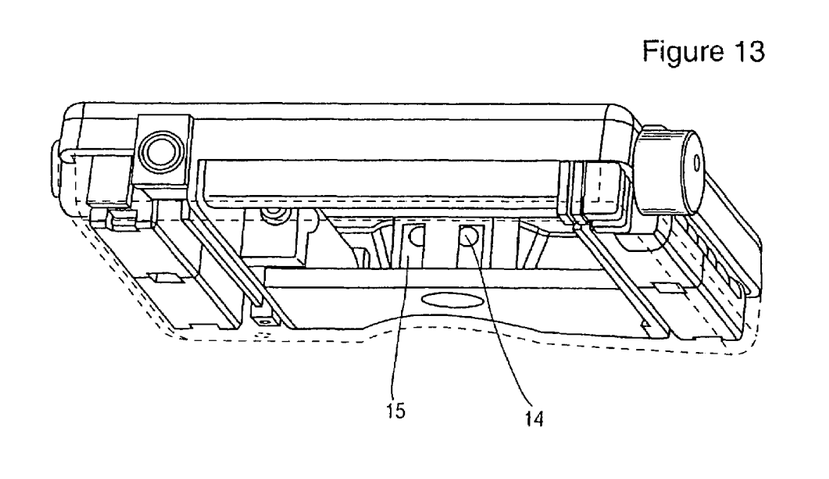
FIG. 13 diagrammatically shows an additional detailed schematic of a preferred embodiment of the present invention.

In FIG. 7 the set with 12 set bolts by invention is formed from the tillable left (13) and right part (14) which can move around the rotation axis (15). We can adjust the distance between the eye (3) of patient (2) and the color-scales (1,1/A) with rotating of the 12 set bolts. We can adjust the eyehole (6) to the patient's (2) eye (3) with moving of the tillable left (13) and right part (14) which are been able to rotate around the rotation axis (15).

In what follows we describe with more details the mechanism of the invention according to the preferred device. The patient (2) moves the set of invention (4) in front of his eye (3) by the eyehole (6). The two eyes see clearly the color-scale 1. The eye of patient which is looking through the opening and the tube perceives the color-scale 1/A. The cause of the tube (7) the eye 3 perceives the same color in a different way as the eye 2 does. Than the patient is moving the color-scale 1 in front of the eye 2 until he will see the same dye perceived by his other eye (3). In that time we read the sign of this dye from the color-scale 1/A named 'NCS Index, edition 2' and we compare it to a list made during the practical measures and find the assigned current blood-glucose level.

FIGS. 8 to 13 describe the invention in further detail from a variety of perspectives.

Although the invention has been described with reference to certain specific embodiments, various modifications thereof will be apparent to those skilled in the art without departing from the spirit and scope of the invention as outlined in the claims appended hereto.

The embodiments of the invention in which an exclusive property or privilege is claimed are defined as follows:

1. A device for measuring blood glucose level comprising:
a box having a cover that can be opened and closed and a side with two openings each covered with a transparent material further including at least two test cards arranged at specified distances and specified positions within the box, and at least one illuminator in the box configured to generate a diffuse beam and positioned therein to illuminate the two test cards wherein light reflected from one of the test cards is directed to a first of said openings and a diffuse beam reflected from the other test card is directed through a tubular prism configured to make diffuse light parallel within 10° that is covered with a closing plate with a first opening at one end while having a second opening aligned with a second of said openings at the other end.

2. Blood glucose level measuring device as in claim 1, characterized by that a plurality of pairs of test cards are fastened on sides of a regular polygonal prism that can be rotated within the blood glucose level measuring device by a turn knob; and further a positioning spring holds the regular polygonal prism in position and a corresponding blood glucose level value is indicated on a dial of the turn-knob.

3. Blood glucose level measuring device as in claim 2, characterized by that only a single pair of test cards is viewable through the openings in the box and the other pairs of test cards are covered by two cover plates in order to eliminate their disturbing effects.

4. Blood glucose level measuring device as in claim 1, characterized by that one of said openings in the box is on a portion adjustable relative to the other opening.

5. Blood glucose level measuring device as in claim 1, characterized by that the illuminator is actuated by a micro switch mounted between two springs fastened to a base plate of the box.

6. Blood glucose level measuring device as in claim 1, characterized by that the diameter D1 of the first opening of the polygonal tubular prism is up to 2 mm, the diameter D2 of the second opening of the polygonal tubular prism and the diameter D4 of the first opening in the box are less than 10 mm each, and further the diameter D3 of the tubular prism is greater than or equal to the diameter D2.

7. Blood glucose level measuring device as in claim 1, characterized by that the distances between each opening in the box and the corresponding test card are equal and the length of the tubular prism is longer than 10mm.

8. Blood glucose level measuring device as in claim 1, characterized by that the illuminator is a glow lamp controlled by a push-button switch or a rotating switch and the illumination is active for a pre-determined time followed by a period where the illumination is disabled for a specified time; the readiness of the device to be switched on again is indicated by an indicator lamp; and further comprising a general switch to turn the device OFF and ON.

9. Blood glucose level measuring device as in claim 1, characterized by that it is provided with a voltage indicator connected to a battery.

10. Blood glucose level measuring device as in claim 1, further including a battery in electrical communication with the at least one illuminator and a connector for recharging the battery.

* * * * *